United States Patent
Pan et al.

(10) Patent No.: US 8,441,080 B2
(45) Date of Patent: May 14, 2013

(54) SENSING DEVICE

(76) Inventors: Tung-Ming Pan, Taipei (TW);
Min-Hsien Wu, Kaohsiung (TW);
Ming-De Huang, Changhua County (TW); Chao-Sung Lai, Taoyuan County (TW)

( * ) Notice: Subject to any disclaimer, the term of this patent is extended or adjusted under 35 U.S.C. 154(b) by 128 days.

(21) Appl. No.: 12/793,647

(22) Filed: Jun. 3, 2010

(65) Prior Publication Data
US 2011/0298015 A1 Dec. 8, 2011

(51) Int. Cl.
*H01L 27/14* (2006.01)
(52) U.S. Cl.
USPC .................................. 257/414; 257/E29.166
(58) Field of Classification Search .................. 257/414, 257/E29.166
See application file for complete search history.

(56) References Cited

U.S. PATENT DOCUMENTS
2006/0102935 A1* 5/2006 Yitzchaik et al. ............. 257/253

OTHER PUBLICATIONS

Jeon et al., "Electrical and physical characteristics of PrTixOy for metal-oxide semiconductor gate dielectric applications," Appl. Phys Lett. 81, 4856 (2002).*
Lyashenko et al, "Conductivity of Sm2TiO5 and Sm2Ti2O7," Inorganic Materials, vol. 44, 12, 1349-1353 (2008).*
Wu, Min-Hsien et al., "Structural properties and sensing performance of high-k Sm2O3 membrane-based electrolyte solution-insulator-semiconductor for pH and urea detection", Sensors and Actuators. B, Chemical, 2009, 138:1, pp. 221-227 (2009).

* cited by examiner

*Primary Examiner* — Matthew Reames
(74) *Attorney, Agent, or Firm* — Hamilton, DeSanctis & Cha LLP

(57) ABSTRACT

A sensing device includes: a semiconductor layer of a field effect semiconductor having upper and lower surfaces; a conductive layer formed on the lower surface of the semiconductor layer; and a sensor layer of an insulator formed on the upper surface of the semiconductor layer. The insulator is made from lanthanide-titanium oxide.

8 Claims, 5 Drawing Sheets

SENSING DEVICE

BACKGROUND OF THE INVENTION

1. Field of the Invention

The invention relates to a sensing device, more particularly to a sensing device including a sensor layer of an insulator made from lanthanide-titanium oxide.

2. Description of the Related Art

Wu Min-Hsien, et. al.; "Structural properties and sensing performance of high-k $Sm_2O_3$ membrane-based electrolyte solution-insulator-semiconductor for pH and urea detection" Sensors and actuators, B: Chemical (ISSN 0925-4005), Volume 138, Issue 1, 24 Apr. 2009, pages 221-227, discloses a conventional sensing device for detecting the concentration of hydrogen ions (pH value) or substances in an electrolyte solution 100. Referring to FIG. 1, the conventional detecting system includes a semiconductor layer 111 of a field effect semiconductor having upper and lower surfaces, a lower electrode 112 formed on the lower surface of the semiconductor layer 111, a sensor layer 113 of the $Sm_2O_3$ membrane formed on the upper surface of the semiconductor layer 111, a protective cover layer 122 partially covering the sensor layer 113 and formed with a through-hole to expose a portion of the sensor layer 113 which is to be in contact with the electrolyte solution 100, and a reference electrode 13 disposed adjacent to the exposed portion of the sensor layer 113 for applying a potential to the exposed portion of the sensor layer 113. In operation, the sensing device is placed in contact with the electrolyte solution 100 with the reference electrode 13 extending into the electrolyte solution 100 and disposed adjacent to the through-hole in the protective cover layer 122, followed by applying different potentials to the reference electrode 13 for obtaining a capacitance-voltage characteristic curve (C-V curve) of the sensing device. The field effect semiconductor can be a p-type or an n-type semiconductor, and is capable of forming a field-induced inversion region of charges (not shown) when a voltage is applied across the reference electrode 13 and the lower electrode 112. The presence of the inversion region in the field effect semiconductor renders the sensing device to possess a characteristic C-V curve which varies with the amount of charges in the inversion region. The concentration of the ions in the electrolyte solution 100 can affect the potential at the sensor layer 113 applied by the reference electrode 13, which, in turn, affects the amount of the charges in the inversion region. As such, an increase or a decrease in the concentration of the ions causes shift of the C-V curve along a direction. Hence, through a measured C-V curve of the sensing device, the concentration of the ions in the electrolyte solution 100 can be determined.

Although the $Sm_2O_3$ membrane of the aforesaid conventional sensing device is capable of providing a stable C-V curve, there is still a need to enhance the detection sensitivity of the sensing device and to reduce the hysteresis voltage and the drift rate of the sensing device.

SUMMARY OF THE INVENTION

Therefore, the object of the present invention is to provide a sensing device that can enhance at least the detection sensitivity of the sensing device.

Accordingly, a sensing device of the present invention comprises: a semiconductor layer of a field effect semiconductor having upper and lower surfaces; a conductive layer formed on the lower surface of the semiconductor layer; and a sensor layer of an insulator formed on the upper surface of the semiconductor layer. The insulator is made from lanthanide-titanium oxide.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
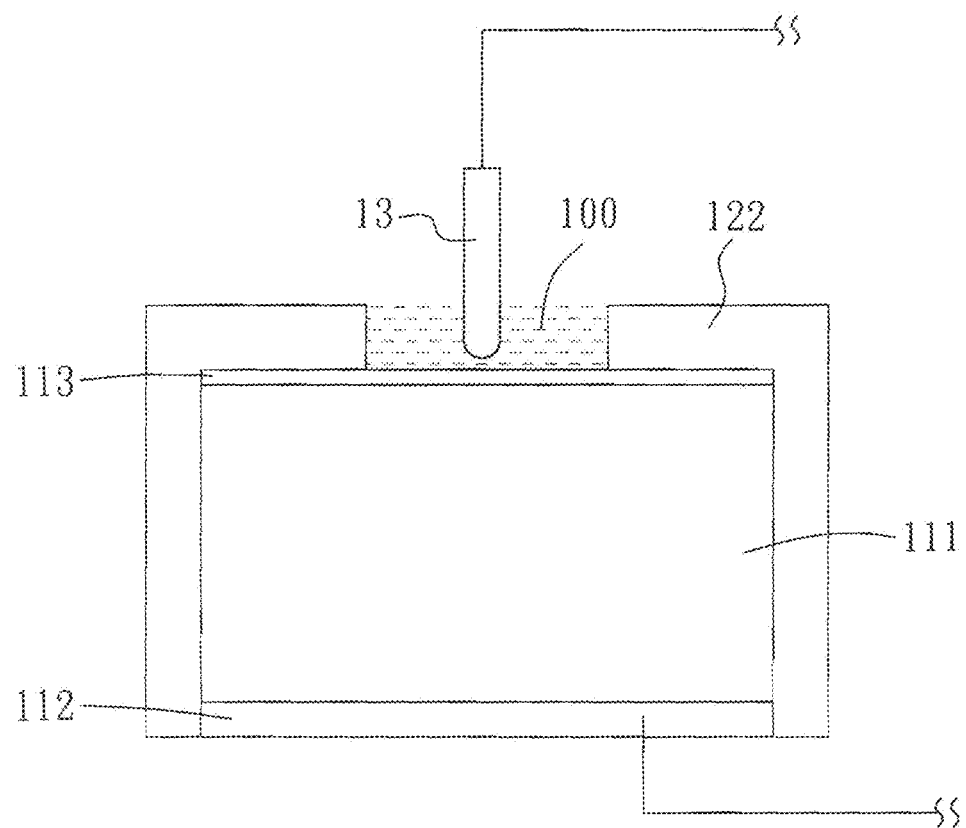
FIG. 1 is a schematic diagram illustrating the configuration of a conventional sensing device.

Before the present invention is described in greater detail with reference to the accompanying preferred embodiments, it should be noted herein that like elements are denoted by the same reference numerals throughout the disclosure.

Figure 2:
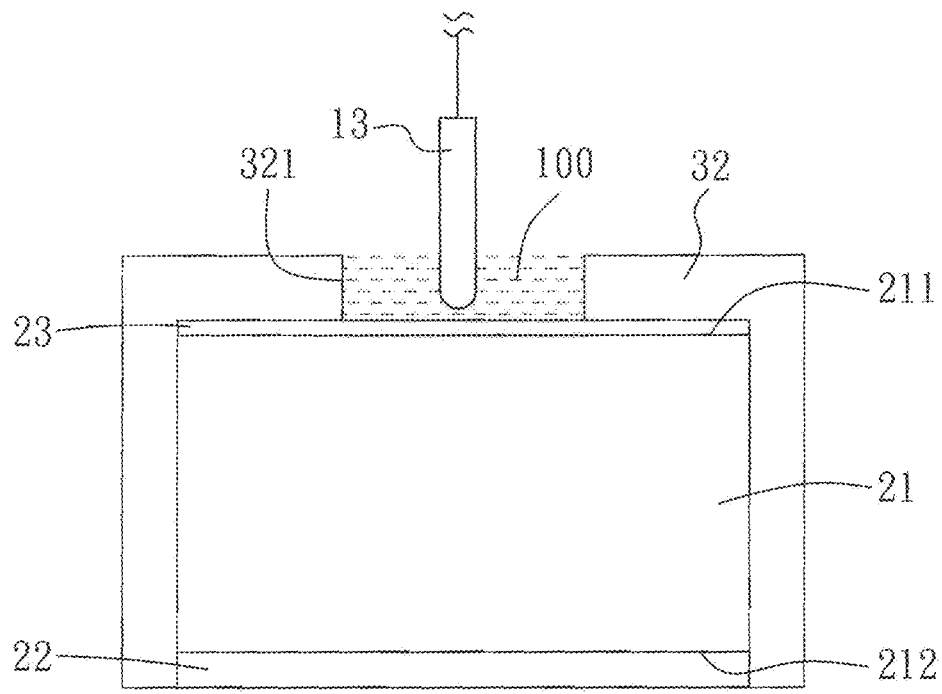
FIG. 2 is a schematic diagram of the first preferred embodiment of a sensing device according to this invention.

FIG. 2 illustrates the first preferred embodiment of a sensing device according to the present invention for detecting the concentration of ions, such as hydrogen ions, or a substance in an electrolyte solution 100. The sensing device includes: a semiconductor layer 21 of a field effect semiconductor having upper and lower surfaces 211, 212; a conductive layer 22 formed on the lower surface 212 of the semiconductor layer 21; a sensor layer 23 of an insulator formed on the upper surface 211 of the semiconductor layer 21, the insulator being made from lanthanide-titanium oxide; and a protective cover layer 32 partially covering the sensor layer 23 and formed with a through-hole 321 to expose a portion of the sensor layer 23 which is to be in contact with the electrolyte solution 100.

The field effect semiconductor is a p-type or an n-type semiconductor, such as p-type or n-type silicon wafer. The lanthanide-titanium oxide of the sensor layer 23 is preferably samarium-titanium oxide ($Sm_2TiO_5$). Other lanthanide elements are also suitable for making the lanthanide-titanium oxide of the sensor layer 23 due to their high dielectric constant, which permits the sensor layer 23 to have a high sensitivity, and high energy gap, which permits the sensor layer 23 to have a low leakage current. The sensor layer 23 preferably has a layer thickness ranging from 3 to 100 nm, and is preferably annealed at an annealing temperature ranging from 700° C. to 1100° C., more preferably, from 700° C. to 900° C.

and most preferably, from 800° C. to 900° C. When the layer thickness of the sensor layer 12 is less than 3 nm, the sensing device can exhibit insufficient tunneling current and capacitance in detection of the ions of interest, which results in distortion or inaccuracy of the measured concentration of the ions. When the layer thickness of the sensor layer 12 is greater than 100 nm, manufacturing costs of the sensing device are considerably increased. When the annealing temperature is less than 700° C., the lanthanide-titanium oxide exhibits a poor crystalline property. When the annealing temperature is greater than 1100° C. the lanthanide-titanium oxide of the sensor layer 23 tends to react with the field effect semiconductor to form an undesired compound, such as Sm-silicate.

The protective cover layer 32 can be formed by applying a photoresist to the assembly of the semiconductor layer 21, the conductive layer 22 and the sensor layer 23, followed by partially removing the photoresist through photolithography techniques to expose the portion of the sensor layer 23 to be in contact with the electrolyte solution 100, and subsequently coating with epoxy resin for covering the remainder of the photoresist.

In operation, the sensing device is brought into contact with a body of the electrolyte solution 100 and a reference electrode 13, such as Ag/AgCl reference electrode, is extended into the body of the electrolyte solution 100, is disposed adjacent to the sensor layer 23 and is connected to a power source (not shown) for applying a potential to one side of the sensor layer 23 so as to measure the C-V curve of the sensing device based on which the pH value of the electrolyte solution 100 can be determined.

Figure 3:
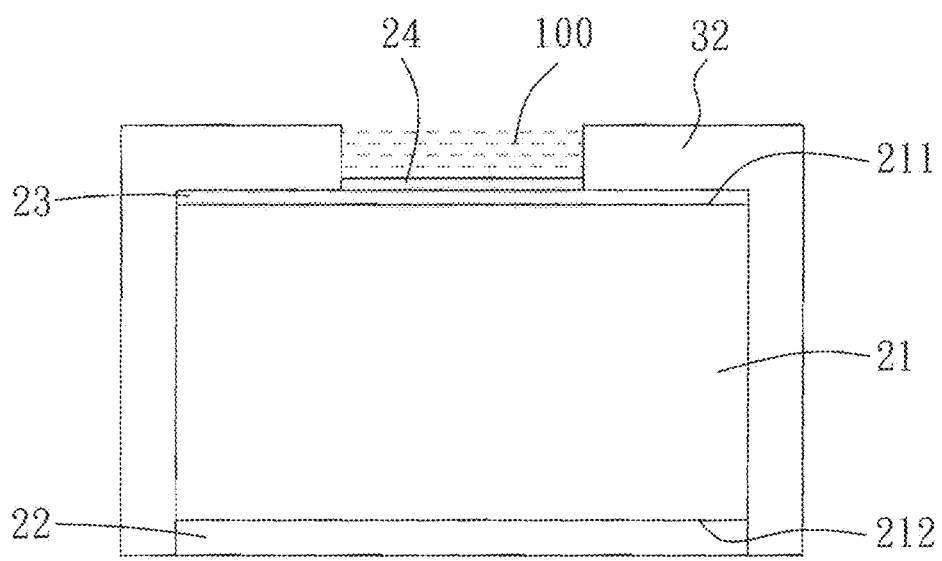
FIG. 3 is a schematic diagram of the second preferred embodiment of a sensing device according to this invention.

FIG. 3 illustrates the second preferred embodiment of the sensing device according to this invention for detecting the concentration of a substance in an electrolyte solution 100. The second preferred embodiment differs from the previous embodiment in that the second preferred embodiment further includes an enzyme layer 24 formed on the sensor layer 23 and containing an enzyme that is capable of reacting with the substance in the electrolyte solution 100. Through reaction between the enzyme and the substance, the pH value of the enzyme layer 24 is changed, which, in turn, results in a change in the potential at the sensor layer 23.

The enzyme layer 24 can be formed on the sensor layer 23 by mixing the enzyme with a solution of alginate gel and calcium chloride to form an enzyme-immobilized calcium alginate hydrogel, followed by application of the enzyme-immobilized calcium alginate hydrogel to the sensor layer 23 and drying. In one preferred embodiment, the enzyme is capable of decomposing glucose or glucan so that the sensing device can be used to determine the concentration of the glucose in the electrolyte solution 100.

The following Examples and Comparative Example are provided to illustrate the merits of the preferred embodiments of the invention, and should not be construed as limiting the scope of the invention.

Example 1

The sensing device of Example 1 has the same configuration as that of the first preferred embodiment, in which the lanthanide-titanium oxide of the sensor layer 23 is samarium-titanium oxide ($Sm_2TiO_5$), the layer thickness of the sensor layer 23 is about 40 nm, and the field effect semiconductor is a p-type silicon wafer.

Example 2

The sensing device of Example 2 has the same configuration as that of the second preferred embodiment, in which the lanthanide-titanium oxide of the sensor layer 23 is samarium-titanium oxide ($Sm_2TiO_5$), the layer thickness of the sensor layer 23 is about 40 nm, the enzyme of the enzyme layer 24 is capable of decomposing glucose, and the field effect semiconductor is a p-type silicon wafer.

Comparative Example

The sensing device of the Comparative Example has a configuration differing from that of Example 1 in that the sensor layer is made from samarium oxide ($Sm_2O_3$).

Figure 4:
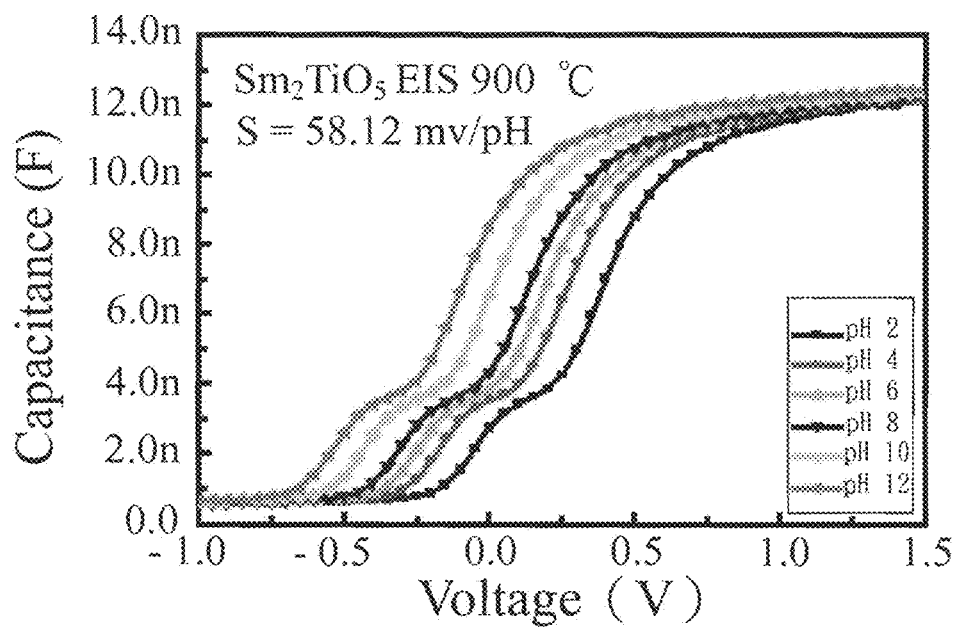
FIG. 4 is a plot of C-V curves of the first preferred embodiment for different concentrations of hydrogen ions (or pH values) in electrolyte solutions.

FIG. 4 is a plot of C-V curves for different pH values of an electrolyte solution. The measurement was conducted using the sensing device of Example 1 and an Ag/Agcl reference electrode which were placed in the electrolyte solution and were coupled to a power source (not shown). The sensor layer 23 was annealed at 900° C. The measured results show that the sensing device of Example 1 exhibits a steady gradual shift of C-V curve from left to right when the pH value of the electrolyte solution is gradually decreased from 12 to 2 (i.e., a gradual increase in the hydrogen ions).

Figure 5:
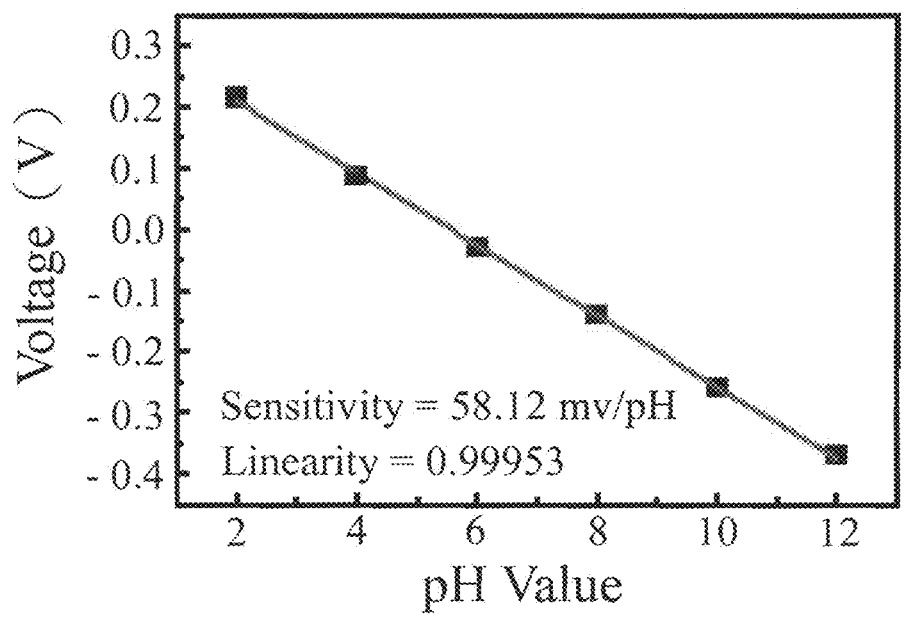
FIG. 5 is a plot of the detection linearity of the first preferred embodiment determined by calculation based on the C-V curves of FIG. 4.

FIG. 5 is a plot showing the detection linearity and the detection sensitivity of the sensing device of Example 1 in the electrolyte solution. The data line in FIG. 5 is determined by calculation based on the C-V curves of FIG. 4. The detection linearity and the detection sensitivity of the sensing device of Example 1 in the electrolyte solution are 0.99953 and 58.12 mV/pH, respectively.

Figure 6:
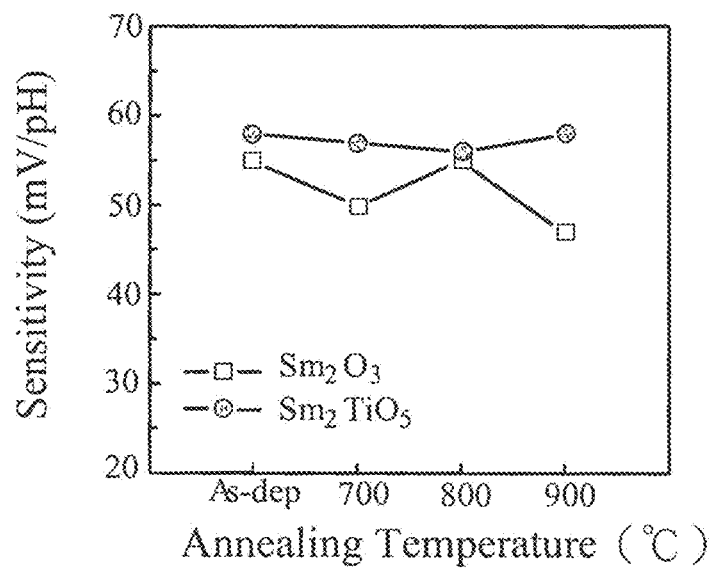
FIG. 6 is a plot to compare the detection sensitivity of the first preferred embodiment with that of the aforesaid conventional sensing device at different annealing temperatures.

FIG. 6 is a plot to compare the detection linearity of the sensing device of Example 1 with that of the sensing device of the Comparative Example in an electrolyte solution for a non-annealing condition (labeled as As-dep in FIG. 6) where the sensing devices of Example 1 and the Comparative Example were not annealed and for different annealing conditions where the sensing devices of Example 1 and the Comparative Example were annealed under 700° C., 800° C., and 900° C., respectively. The results show that the sensing device of Example 1 has a higher detection linearity than that of the sensing device of the Comparative Example.

Figure 7:
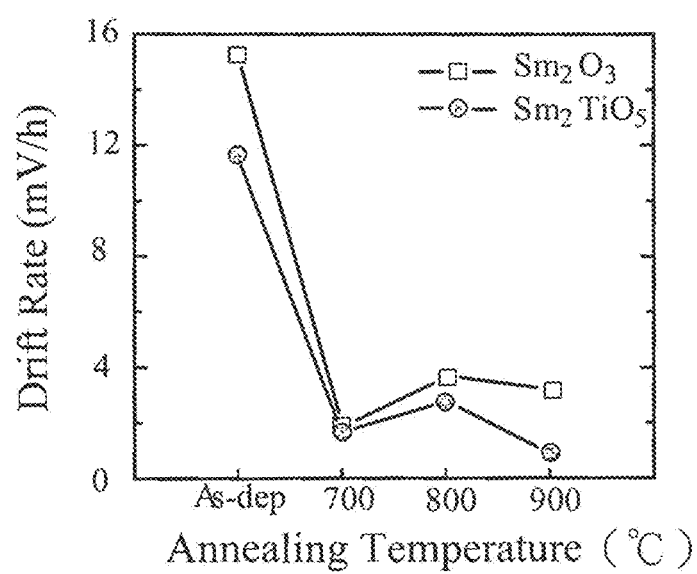
FIG. 7 is a plot to compare the drift rate of the first preferred embodiment with that of the aforesaid conventional sensing device at different annealing temperatures.

FIG. 7 is a plot to compare the drift rate of the sensing device of Example 1 with that of the sensing device of the Comparative Example in an electrolyte solution for a non-annealing condition (labeled as As-dep in FIG. 7) where the sensing devices of Example 1 and the Comparative Example were not annealed and for annealing conditions where the sensing devices of Example 1 and the Comparative Example were annealed under 700° C., 800° C., and 900° C., respectively. The results show that the sensing device of Example 1 has a lower drift rate than that of the sensing device of the Comparative Example.

Figure 8:
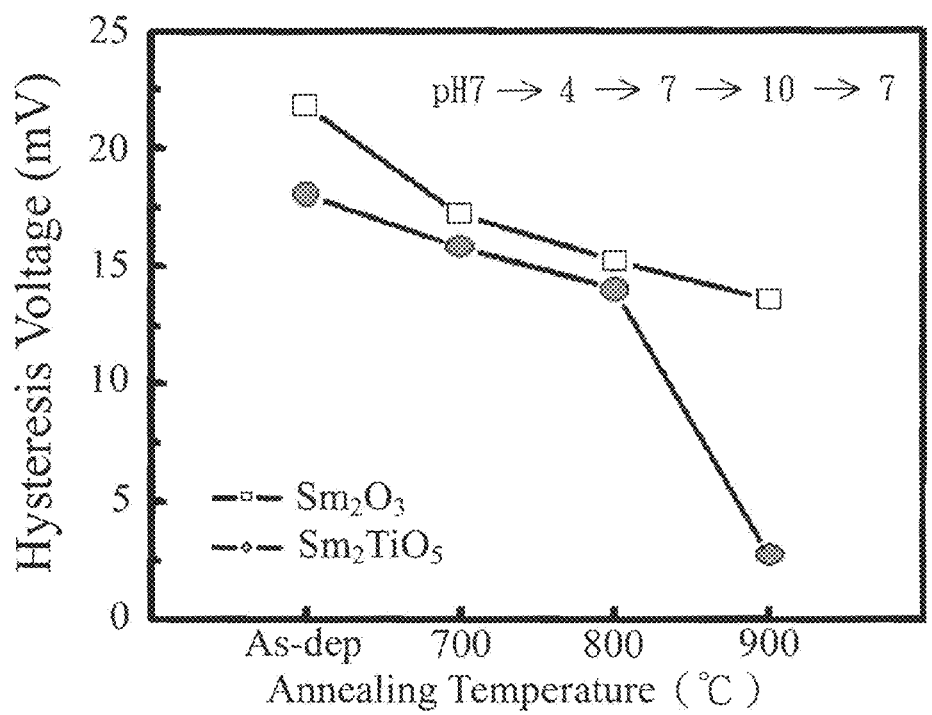
FIG. 8 is a plot to compare the hysteresis voltage of the first preferred embodiment with that of the aforesaid conventional sensing device at different annealing temperatures.

FIG. 8 is a plot to compare the hysteresis voltage of the sensing device of Example 1 with that of the sensing device of the Comparative Example in an electrolyte solution containing hydrogen ions for a non-annealing condition (labeled as As-dep in FIG. 8) where the sensing devices of Example 1 and the Comparative Example were not annealed and for annealing conditions where the sensing devices of Example 1 and the Comparative Example were annealed under 700° C., 800° C. and 900° C., respectively. The results show that the sensing device of Example 1 has a lower hysteresis voltage than that of the sensing device of the Comparative Example. It is noted that a great reduction of the hysteresis voltage is achieved for the sensing device of Example 1 as compared to the Comparative Example when the annealing temperature is greater than 800° C.

Figure 9:
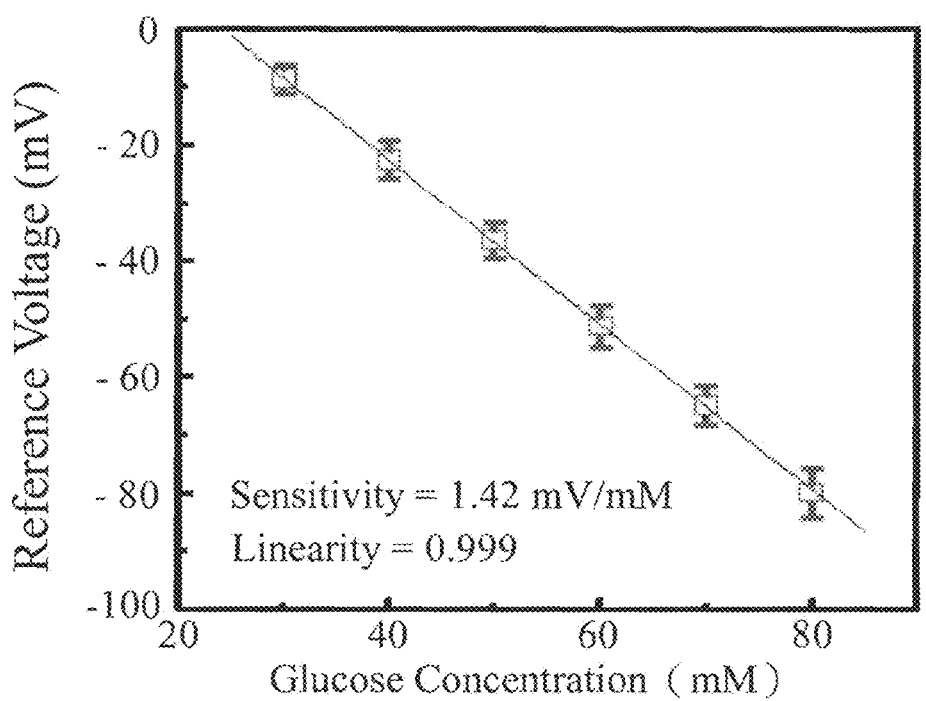
FIG. 9 is a plot of the detection linearity of the second preferred embodiment.

FIG. 9 is a plot showing the detection linearity and the detection sensitivity of the sensing device of Example 2 in an electrolyte solution containing glucose. The data line in FIG. 9 is determined by a manner similar to that of FIG. 5. The detection linearity and the detection sensitivity of the sensing device of Example 2 in the electrolyte solution are 0.999 and 1.42 mV/mM, respectively.

Compared to the conventional sensing device using samarium oxide for making the sensor layer, the sensing device of this invention using the lanthanide-titanium oxide for making the sensor layer 23 exhibits an improvement in the detection sensitivity and in the hysteresis voltage and the drift rate.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A sensing device comprising:
   a semiconductor layer of a field effect semiconductor having upper and lower surfaces;
   a conductive layer formed on said lower surface of said semiconductor layer; and
   a sensor layer of an insulator formed on said upper surface of said semiconductor layer;
   wherein said insulator is made from lanthanide-titanium oxide; and
   wherein said insulator exhibits at 900° C. a higher detection sensitivity not less than 58.12 mV/pH, a lower drift rate not higher than 2 mV/h, and a lower hysteresis voltage not higher than 5 when compared to an insulator made from $Sm_2O_3$.

2. The sensing device of claim 1, wherein said lanthanide-titanium oxide is samarium-titanium oxide.

3. The sensing device of claim 1, further comprising an enzyme layer formed on said sensor layer and containing an enzyme.

4. The sensing device of claim 1, wherein said lanthanide-titanium oxide is annealed under a temperature ranging from 700° C. to 1100° C.

5. The sensing device of claim 4, wherein said lanthanide-titanium oxide is annealed under a temperature ranging from 700° C. to 900° C.

6. The sensing device of claim 5, wherein said lanthanide-titanium oxide is annealed under a temperature ranging from 800° C. to 900° C.

7. The sensing device of claim 1, wherein said semiconductor layer is one of a p-type semiconductor and an n-type semiconductor.

8. The sensing device of claim 1, wherein said sensor layer has a layer thickness ranging from 3 to 100 nm.

* * * * *

UNITED STATES PATENT AND TRADEMARK OFFICE
CERTIFICATE OF CORRECTION

PATENT NO.         : 8,441,080 B2
APPLICATION NO.    : 12/793647
DATED              : May 14, 2013
INVENTOR(S)        : Tung-Ming Pan et al.

Page 1 of 1

It is certified that error appears in the above-identified patent and that said Letters Patent is hereby corrected as shown below:

Title Page: Item 76 should be changed to 75

Title Page: Item 73 should read:

Assignee: Chang Gung University, Tao-Yuan Taiwan

Signed and Sealed this
Eighteenth Day of February, 2014

Michelle K. Lee
*Deputy Director of the United States Patent and Trademark Office*